United States Patent
Kumar et al.

US007459467B2

(10) Patent No.: US 7,459,467 B2
(45) Date of Patent: Dec. 2, 2008

(54) MANUFACTURING PROCESS FOR METHYL PHENIDATE AND INTERMEDIATES THEREOF

(75) Inventors: Ashok Kumar, Mumbai (IN); Dharmendra Singh, Thane (IN); Swapnali Hemant Patil, Thane (IN); Ganesh Devidas Mahale, Mumbai (IN); Uttamrao Arjunrao Sawant, Thane (IN)

(73) Assignee: IPCA Laboratories, Ltd., Mumbai (IN)

( * ) Notice: Subject to any disclaimer, the term of this patent is extended or adjusted under 35 U.S.C. 154(b) by 339 days.

(21) Appl. No.: 11/150,737

(22) Filed: Jun. 10, 2005

(65) Prior Publication Data
US 2005/0277667 A1 Dec. 15, 2005

(30) Foreign Application Priority Data
Jun. 15, 2004 (IN) .................................. 651/2004

(51) Int. Cl.
*A61K 31/4458* (2006.01)
*C07D 211/34* (2006.01)

(52) U.S. Cl. ........................ 514/331; 514/317; 546/238; 546/233

(58) Field of Classification Search ................. 514/317, 514/331; 546/342, 185, 238, 233
See application file for complete search history.

(56) References Cited

U.S. PATENT DOCUMENTS 2,957,880 A * 10/1960 Rometsch .................... 546/233

OTHER PUBLICATIONS

Deutsch et al., J. Med. Chem., 1996, 39, 1201-1209.*
Freifelder, J. Org. Chem.,1964, 29(10), 2895-2898.*
Chung et al., J. Org. Chem.,1996, 61, 215-222.*
Zacharie et al. (J. Org. Chem.,2001, 66, 5264-5265.*

* cited by examiner

*Primary Examiner*—Bernard Dentz
*Assistant Examiner*—David E Gallis
(74) *Attorney, Agent, or Firm*—Blank Rome LLP

(57) ABSTRACT

The present invention discloses selective and complete reduction of pyridine ring in a biaryl system comprising ∝-substituted or non-substituted benzene ring and relates more specifically, not exclusively, for the manufacture of methylphenidate, which is used for treatment of Attention Deficit Hyperactive Disorder (ADHD) and also acts as central nervous system stimulant, by using palladium/C in a solvent such as C1-C4 alcohols in presence of molar quantities of organic and/or inorganic acids.

16 Claims, No Drawings

MANUFACTURING PROCESS FOR METHYL PHENIDATE AND INTERMEDIATES THEREOF

RELATED APPLICATIONS

This application claims priority from India National Application Serial No. 651/MUM/2004, filed 15 Jun., 2004, incorporated here by reference.

BACKGROUND

The present invention relates to selective reduction of pyridine ring in a biaryl system comprising a—substituted or non substituted benzene ring. This invention further relates more specifically, not exclusively, to the manufacture of methylphenidate or its derivatives or salts.

Biaryl compounds of Formula I (wherein $R=CONR_1R_2$, $COOCH_3$, $COOH$; $X=H$, $Cl$, $Br$, $OMe$, $NH_2$; $R_1R_2=H$ or $C_1$-$C_3$ alkyl groups), specifically substituted $\alpha$-phenyl-$\alpha$-pyridyl-2-acetic acid and its derivatives such as amide, ester are the key intermediates, in the preparation of pharmaceutical drug methylphenidate (Formula II, wherein $R=COOCH_3$; $X=H$) and its acid addition salts. Methylphenidate is used for the treatment of Attention Deficit Hyperactive Disorder (ADHD). Methylphenidate is also used as central nervous system stimulant

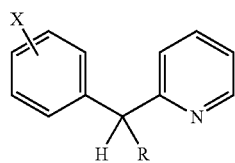

Formula I

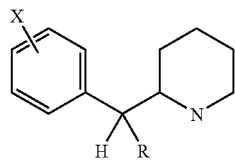

Formula II

Methylphenidate is prepared by the selective reduction of the pyridine ring of a biaryl derivative of Formula I. Methods of such reduction of Formula I are reported in prior art.

In the prior art, U.S. Pat. No. 2,507,631 describes a process according to which catalytic hydrogenation of $\alpha$-phenyl-$\alpha$-pyridyl-2-acetic acid methyl ester was carried out in glacial acetic acid medium in presence of platinum metal catalyst at room temperature to get $\alpha$-phenyl-$\alpha$-piperidyl-2-acetic acid methyl ester and the methyl ester was subsequently hydrolyzed to give the $\alpha$-phenyl-$\alpha$-piperidyl-2-acetic acid.

In another prior art, U.S. Pat. No. 2,957,880, a similar process was disclosed where hydrogenation of 75 parts by weight of $\alpha$-phenyl-$\alpha$-pyridyl-2-acetamide with hydrogen was carried out in glacial acetic acid as solvent in the presence of 1 part by weight of platinum oxide at 40° C. According to '880 patent, the reaction took 26 hours for completion. The product was isolated by evaporating acetic acid and basifying the reaction mass with aqueous NaOH. The process was exemplified for $\alpha$-phenyl $\alpha$-piperidyl-2-acetamide.

Further, a similar process was disclosed in Journal of Medicinal Chemistry 1981, Vol. (24), (10), 1237-1240. In the process, according to this disclosure, Erythro-dl- and threo dl-2-(4-methoxy phenyl)-2-(2'-pyridyl) acetamide hydrochloride (1.1 gm, 4.5 mmol) was dissolved in 15 ml of glacial acetic acid and 50 mg of $PtO_2$ was added. The mixture was placed under slight positive pressure of hydrogen and stirred until the hydrogen uptake ceased. The reaction mixture was filtered and evaporated under reduced pressure to get oil, which was then further purified. The 2-(4-methoxy phenyl)-2-(2'-piperidyl) acetamide obtained was further converted to methylphenidate.

Yet another process, published in Journal of Medicinal Chemistry 1996, Vol. (39), (6), 1201-1209, teaches catalytic hydrogenation of a solution of 0.43 gm (1.7 mmole) of 3-chlorophenyl pyridyl acetamide in 15 ml of acetic acid and 0.14 gm of 5% Platinum on carbon at 30-40° C. for 10 hrs. The catalyst was removed by filtration and the solvent acetic acid was evaporated to dryness, excess concentrated hydrochloric acid was added, further evaporated to dryness to give hydrochloride of 3-chlorophenyl-2-piperidyl acetamide hydrochloride.

A major drawback of the processes described in above documents is that they all use costly catalyst such as platinum metal adsorbed on carbon or platinum oxide with a very high loading [loading means higher amounts with respect to the starting compound (II)] for the selective reduction of pyridine ring. Platinum catalysts are known for their high catalytic activity in comparison with other milder metal catalyst such as Nickel or Palladium. The order of catalytic activity is Rh>Pt>Pd>Ni. By using Pt or its oxide, Platinum oxide catalyst for hydrogenation makes the process less economical. None of these processes describe the use of other less active and less costly catalysts such as Pd or Ni. Another major drawback is the impurity generation due to reduction of the benzene ring, when using platinum metal for selective reduction of pyridine ring in presence of a benzene ring. Since platinum catalysts are known for reduction of aryl rings.

Another drawback of the prior art processes is related to the use of acetic acid as a solvent. The use of these reactive solvents as a medium for reaction is resulted in impurity generation & difficulty in isolation of the product from acetic acid. It is observed that all the prior art processes used acetic acid as solvent. The use of acetic acid is required to protonate the Nitrogen atom on the pyridine rings. The use of acetic acid in reaction as solvent also generate impurities but it goes to higher level when acetic acid is distilled to isolate the product at high temperature. The product as such is difficult to isolate from the acetic acid solution because of solubility problems and makes the process and its operation less plant friendly. Since the final compound is a pharmaceutical drug, the reduction of impurities up to accepted limits also requires additional purification steps, responsible for the substantial yield losses and thereby proportional increase in the cost.

Thus there is a need in the art to discover a process with a milder and economic catalyst for the reduction of compound I and this becomes the subject of the present invention.

OBJECTIVES

1) The main objective of the present invention is to develop a process for the hydrogenation of the heterocyclic ring selectively in presence of (un)substitued benzene ring(s) in a biaryl system of formula I with a moderately active catalyst viz. palladium catalyst.

2) Another objective of the present invention is to provide a process wherein problems associated with the impurity generation and isolation of the compound of formula II are reduced or completely minimized.

3) Yet another objective of the present invention is to provide a simple, economical and plant friendly process for the manufacture of ∝-phenyl-∝-piperdinyl-2-acetic acid and their derivatives thereof.

4) Further object of the present invention is to provide a process specifically for the manufacture of the pharmaceutical compound, methylphenidate, in high yield and purity on an industrial scale.

SUMMARY

Accordingly, the present invention discloses a selective and complete reduction of pyridine ring in a compound of formula I with the use of a moderately active catalyst viz. Palladium on carbon in a solvent such a $C_1$-$C_4$ alcohols in the presence of molar quantities of organic and/or inorganic acid.

In another aspect, the invention provides a specific process for preparation of methylphenidate by the selective reduction of pyridine ring of compound of Formula I, wherein R=COOCH$_3$, COOH, CONR$_1$R$_2$; X=H; R$_1$R$_2$=H or C$_1$-C$_3$ alkyl groups, to form a compound of Formula II, wherein R, X, R$_1$R$_2$ have the same meaning as defined above. The resulting Compound of Formula II (where R=COOH or CONR$_1$R$_2$) is then converted into methyl ester of Formula II by methods known in the art.

In a further aspect, the present invention relates to methyl phenidate prepared according the reduction of compound of Formula II using a palladium catalyst as setout in the present description.

DESCRIPTION

The present invention relates to a process for selective reduction of pyridine ring in substituted ∝-phenyl-∝-pyridyl derivatives of Formula I, wherein R and X has the following meanings.

In the srtucture Formula I, R denotes CONR$_1$R$_2$, COOCH$_3$, COOH; and X=H, Cl, Br, OMe, NH$_2$ wherein, R$_1$ & R$_2$ are independently hydrogen, C$_1$-C$_3$ alkyl groups that include all isomeric forms (isomeric forms means straight chain or branched chain carbon, e.g., isopropyl). Consequently, the invention further involves the manufacture of methylphenidate of the Formula II wherein R=COOCH$_3$; X=H by the reduction of a compound of Formula I wherein R=CONR$_1$R$_2$, COOCH$_3$, COOH; X=H where R$_1$R$_2$ are as defined above, which are important intermediates for the production of methylphenidate. The suitable catalyst for the above reduction is selected from Palladium.

In accordance with the above basic objective of the present invention, suitable procedure for reduction is that ∝-phenyl-∝-pyridyl derivative of Formula I which is suspended in C$_1$-C$_4$ straight or branched chain alcoholic solvents in the presence of equimolar amounts of organic and/or inorganic acids using a palladium catalyst. Equi-molar quantity of acid is used only to protonate the Nitrogen atom on the pyridine ring. Representative example of solvents used are methanol, ethanol, isopropanol etc. and the molar quantities of acids used to protonate the pyridine ring are selected from, but not limited to, sulfuric acid, hydrochloric acid, acetic acid, perchloric acid, phosphoric acid or their combination thereof. Although the selection of a particular acid is not critical to the success of the invention, acetic acid and perchloric acid are preferred.

In a typical procedure, Palladium on carbon is added to the suspended reaction mixture (compound I in alcoholic solvent) and the reaction proceeds at a temperature from room temperature to 70° C. under hydrogen pressure of 5 kg/cm$^2$ to 15 kg/cm$^2$ and completes in 15 to 30 hrs. The palladium on carbon of various capacity used in the present invention are 5% to 10%, although not critical but for economic reasons 5% palladium is preferred. The duration of completion of reaction depends on the parameters such as temperature, hydrogenation pressure etc. known to those skilled in the art. The reaction is advantageously carried out in methanol.

After completion of the reaction the catalyst was removed by filtration and the filtrate was advantageously concentrated by distilling the solvent alcohol under reduced pressure for recovery of solvent and the obtained residue, contains catalytic amount of acid used in the reaction, was diluted with water, basified with aqueous alkili solution to isolate the product of Formula II (wherein R=CONR$_1$R$_2$, COOCH$_3$, COOH; X=H, Cl, Br, OMe, NH$_2$; R$_1$R$_2$=H or C$_1$-C$_3$ alkyl groups).

The catalyst used in the hydrogenation reaction of ∝-phenyl-∝-pyridyl-2-acetic acid and their derivatives of Formula I is, more specifically, 5% Palladium on carbon (50% wet). Catalyst quantity varies from 10 to 15 gm per 100 gm of the starting ∝-phenyl-∝-pyridyl-2-acetic acid derivative.

The suitable volume of solvent for carrying out the hydrogenation varies from 5.0 times to 20 times and more preferably 10 to 12 times but not critical. The optimum hydrogenation temperature ranges from 35°-70° C. and preferably at 45°-50° C. is good enough to get consistent result. A range of the hydrogen pressure from 5-15 kg/cm$^2$ seems to work well but from 10-12 kg/cm$^2$ can be considered to be more preferred to carry out the transformation under consideration.

The compound of Formula II, wherein R=CONR$_1$R$_2$, COOCH$_3$, COOH; X=H obtained by the above reduction process are converted to methylphenidate of Formula II wherein R=COOCH$_3$; X=H by methods known in the art like esterification or hydrolysis and esterification of compound of Formula II etc.

The methylphenidate base obtained after the work-up is converted to its pharmaceutically acceptable acid salts such as hydrochloride by conventional method, which can be suitably incorporated in any conventional dosage form for administering to human patients. Conventional dosage forms include tablets, capsules, injectibles, lozenges etc.

The following non-limiting examples illustrate the invention but are to be construed as illustrative and are meant to cover all the permutations obvious to a person skilled in the art.

EXAMPLES

1) α-Phenyl-α-piperidyl-2-acetamide

In a reaction vessel, 100 gm, α-phenyl-α-pyridyl-2-acetamide, 100 ml of 0.1 N perchloric acid in acetic acid, 10 gm of 5% Pd/C (50% wet) and 1.0 liter methanol were taken together and heated to 45-50.degree. C. under 12-15 Kg/cm.sup.2 hydrogen pressure for 15 to 18 hrs. The catalyst was removed by filtration. Filtrate was concentrated under reduced pressure and concentrated mass was diluted with water and basified with aqueous sodium hydroxide solution to precipitate 95 gm α-phenyl-α-piperidyl-2-acetamide.

Yield of product=95 gm (92.95%).

2) α-Phenyl-α-piperidyl-2-methyl acetate

In a reaction vessel, a mixture of 100 gm α-phenyl-α-pyridyl-2-methyl acetate, 100 ml of 0.1 N perchloric acid in acetic acid in presence of 10 gm 5% Pd/C (50% wet) and 1000 ml methanol were heated to 45-50.degree. C. under 12-15

Kg/cm.sup.2 hydrogen pressure for 15 to 18 hrs. The catalyst was rem by filtration. Filtrate was concentrated under reduced pressure and the concentrated mass was diluted with water and basified with aqueous sodium hydroxide solution to get the product α-phenyl-α-piperidyl-2-methyl acetate.

Yield of product=92 gm (89.88%).

3) Methylphenidate Hydrochloride

In a reaction vessel, 100 gm methylphenidate, 1000 ml isopropyl alcohol were mixed at 30 to 35° C., cool the mixture to 10 to 15° C. To this mixture Isopropanol hydrochloride solution (18-20% HCl (dry) in isopropyl alcohol) was added by maintaining the reaction mass below 15° C. This was maintained for about 5 hours at 30° C., cooled to 10° C. and filtered to isolate methylphenidate hydrochloride. The precipitate was washed with isopropyl alcohol and dried at 60 to 70° C.

Yield was 88 gm (78%)
M. P.=224-226° C.

We claim:

1. A process for reduction of a compound corresponding to the general Formula I, wherein R denotes $CONR_1R_2$, $COOCH_3$, or COOH; X denotes hydrogen, Cl, Br, Ome, or $NH_2$; $R_1$ & $R_2$ are independently Hydrogen or $C_1$-$C_3$ alkyl groups,

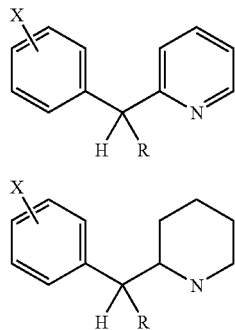

Formula I

Formula II said method comprises the steps of:
 a) preparing a reaction mixture by mixing
  i) a compound of Formula I, wherein R, X, $R_1$ & $R_2$ are as defined above,
  ii) an organic or inorganic acid,
  iii) one or more alcoholic solvent, and
  iv) palladium catalyst: and
 b) effectuating reduction of said reaction mixture in a hydrogen atmosphere to produce a reaction mass comprising compound of Formula II.

2. The process as claimed in claim 1 wherein, said alcohol (s) is selected from $C_1$-$C_4$ straight or branched chain alcoholic solvents.

3. The process as claimed in claims 1 wherein, said alcohol (s) is methanol, ethanol, propanol and isopropanol.

4. The process as claimed in claim 1, wherein said organic and/or inorganic acids includes sulfuric acid, hydrochloric acid, acetic acid, perchioric acid, phosphoric acid or their combination thereof.

5. The process as claimed in claim 1 or 4, wherein the organic/inorganic acid is in molar equivalent amounts relative to compound of Formula I.

6. The process as claimed in claim 1, wherein the said palladium catalyst is 5% to 10% palladium adsorbed on carbon.

7. The process as claimed in claim 1, wherein the said palladium catalyst is 5% palladium adsorbed on carbon.

8. The process as claimed in claim I, wherein the reaction is carried out at a temperature of 35° C. to 70° C. and a hydrogenation pressure of 5 kg/cm² to 15 kg/cm².

9. The process as claimed in claim 1, wherein R is —$CONH_2$, —$COOCH_3$, —COOH and X is Hydrogen.

10. The process as claimed claim 1 wherein compound of Formula II is methylphenidate.

11. The process as claimed in claim 10, wherein the methylphenidate is further converted to its hydrochloride salt.

12. A process for preparation of methylphenidate or a derivative or a salt thereof comprising a step of reducing a compound of Formula I in presence of a palladium catalyst

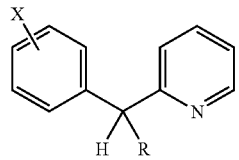

Formula I wherein R denotes $CONR_1R_2$, $COOCH_3$, or COOH; X denotes hydrogen, Cl, Br, OMe, or $NH_2$;
 $R_1$ & $R_2$ are independently Hydrogen or $C_1$-$C_3$ alkyl groups.

13. The process of claim 12, wherein the step of reducing the compound of Formula I comprises
 a) preparing a reaction mixture by mixing
  i) a compound of Formula I, wherein R, X, $R_1$ & $R_2$ are as defined above,
  ii) an organic or inorganic acid,
  iii) one or more alcoholic solvent, and
  iv) palladium catalyst: and
 b) effectuating reduction of said reaction mixture in a hydrogen atmosphere to produce a reaction mass comprising compound of Formula II.

14. The process of claim 12, further comprising step of forming a pharmaceutical dosage form, wherein the dosage form comprises the methylphenidate.

15. The process as claimed in claim 14, wherein the dosage form comprises the methylphenidate or its hydrochloride salt and a diluent or carrier.

16. The process of claim 13, further comprising reacting the compound of Formula II to produce methylphenidate or a derivative or a salt thereof.

* * * * *